(12) United States Patent
Almeida

(10) Patent No.: US 7,097,639 B1
(45) Date of Patent: Aug. 29, 2006

(54) DUAL FILTER MULTIPLE PULSE PHOTO-DERMATOLOGICAL DEVICE WITH PRE/POST OPTICAL HEATING, QUASI-LOGARITHMIC SPACING, AND LASER ROD SPECTRUM INFUSION

(75) Inventor: Stephen Almeida, Tampa, FL (US)

(73) Assignee: Zian Medical, LLC, Tampa, FL (US)

( * ) Notice: Subject to any disclaimer, the term of this patent is extended or adjusted under 35 U.S.C. 154(b) by 138 days.

(21) Appl. No.: 10/600,176

(22) Filed: Jun. 20, 2003

Related U.S. Application Data

(63) Continuation-in-part of application No. 09/841,816, filed on Apr. 25, 2001, now Pat. No. 6,595,986, which is a continuation-in-part of application No. 09/173,422, filed on Oct. 15, 1998, now Pat. No. 6,228,074.

(51) Int. Cl.
*A61B 18/18* (2006.01)
*A61N 5/06* (2006.01)

(52) U.S. Cl. .................. 606/9; 606/3; 606/10; 607/88; 607/91; 128/898

(58) Field of Classification Search .................... 606/3, 606/9, 10; 607/88–91; 128/898
See application file for complete search history.

(56) References Cited

U.S. PATENT DOCUMENTS

| | | | | |
|---|---|---|---|---|
| 4,388,924 A | 6/1983 | Weissman et al. | ....... | 128/303.1 |
| 5,000,752 A | 3/1991 | Hoskin | ........... | 606/9 |
| 5,226,907 A | 7/1993 | Tankovich | ......... | 606/133 |
| 5,282,842 A * | 2/1994 | Changaris | ......... | 607/88 |
| 5,405,368 A | 4/1995 | Eckhouse | ........... | 607/88 |
| 5,425,728 A | 6/1995 | Tankovich | ......... | 606/9 |
| 5,425,754 A * | 6/1995 | Braun et al. | ........ | 607/88 |
| 5,474,549 A | 12/1995 | Ortiz et al. | ........... | 606/9 |
| 5,486,172 A | 1/1996 | Chess | ........... | 606/20 |
| 5,558,667 A | 9/1996 | Yarborough et al. | .......... | 606/9 |
| 5,595,568 A | 1/1997 | Anderson et al. | ........... | 660/9 |
| 5,620,478 A * | 4/1997 | Eckhouse | ........ | 607/88 |
| 5,626,631 A | 5/1997 | Eckhouse | ........ | 607/88 |
| 5,628,744 A | 5/1997 | Coleman et al. | ........... | 606/12 |
| 5,630,811 A | 5/1997 | Miller | ........... | 606/9 |
| 5,632,741 A | 5/1997 | Zavislan et al. | ........... | 606/9 |
| 5,643,334 A | 7/1997 | Eckhouse et al. | ........... | 607/88 |
| 5,647,866 A | 7/1997 | Zaias et al. | ........... | 606/9 |
| 5,683,380 A * | 11/1997 | Eckhouse et al. | ........... | 606/9 |
| 5,720,772 A | 2/1998 | Eckhouse | ........ | 607/88 |
| 5,735,844 A | 4/1998 | Anderson et al. | ........... | 606/9 |
| 5,752,948 A | 5/1998 | Tankovich et al. | ........... | 606/9 |
| 5,752,949 A | 5/1998 | Tankovich et al. | ........... | 606/9 |

(Continued)

*Primary Examiner*—A. Farah
(74) *Attorney, Agent, or Firm*—Brown Rudnick Berlack Israels LLP; John C. Serio

(57) ABSTRACT

Method and apparatus to treat unwanted dermatological conditions on a specific area of the body. The area of treatment is exposed to a specific pattern of multi-wavelength light which may have an added infusion of a particular wavelength from a unique non-collimated laser rod optical insertion. The light is generated by specific gas mixture multiple flashlamps that allow simultaneous, overlap, or consecutive firing with quasi-logarithmic spacing between pulses. Pre/Post low level optical heating increases lesion temperature to optimize pulsed treatment. The optimum fixed specific wavelength distribution pattern allows the treatment of various skin conditions by adjusting the intensity of light, and delay between pulses. The need for skin cooling and damage to skin treatment areas is eliminated by the quasi-logarithmic pulse spacing in conjunction with optimum length and characteristic shape of the individual pulses of light.

20 Claims, 17 Drawing Sheets

U.S. PATENT DOCUMENTS

| | | | |
|---|---|---|---|
| 5,755,751 A | 5/1998 | Eckhouse | 607/88 |
| 5,766,214 A | 6/1998 | Mehl, Sr. et al. | 606/9 |
| 5,776,175 A | 7/1998 | Eckhouse et al. | 607/100 |
| 5,810,801 A | 9/1998 | Anderson et al. | 606/9 |
| 5,828,803 A | 10/1998 | Eckhouse | 385/88 |
| 5,833,612 A | 11/1998 | Eckhouse et al. | 600/476 |
| 5,836,999 A * | 11/1998 | Eckhouse et al. | 607/88 |
| 5,849,029 A | 12/1998 | Eckhouse et al. | 607/104 |
| 5,868,732 A | 2/1999 | Waldman et al. | 606/9 |
| 5,885,273 A | 3/1999 | Eckhouse et al. | 606/9 |
| 5,885,274 A | 3/1999 | Fullmer et al. | 606/9 |
| 5,911,718 A | 6/1999 | Yarborough et al. | 606/9 |
| 5,961,543 A | 10/1999 | Waldmann | 607/88 |
| 5,964,749 A | 10/1999 | Eckhouse et al. | 606/9 |
| 6,050,990 A | 4/2000 | Tankovich et al. | 606/9 |
| 6,120,497 A | 9/2000 | Anderson et al. | 606/9 |
| 6,126,655 A | 10/2000 | Domankevitz et al. | 606/17 |
| 6,161,544 A | 12/2000 | DeVore et al. | 128/898 |
| 6,162,212 A | 12/2000 | Kreindel et al. | 606/9 |
| 6,168,590 B1 | 1/2001 | Neev | 606/9 |
| 6,174,325 B1 | 1/2001 | Eckhouse | 607/88 |
| 6,187,001 B1 | 2/2001 | Azar et al. | 606/9 |
| 6,214,034 B1 | 4/2001 | Azar | 607/89 |
| 6,228,074 B1 * | 5/2001 | Almeida | 606/9 |
| 6,273,884 B1 | 8/2001 | Altshuler et al. | 606/9 |
| 6,280,438 B1 | 8/2001 | Eckhouse et al. | 606/9 |
| 6,306,130 B1 * | 10/2001 | Anderson et al. | 606/27 |
| 6,350,261 B1 | 2/2002 | Domankevitz et al. | 606/17 |
| 6,447,537 B1 | 9/2002 | Hartman | 607/94 |
| 6,517,532 B1 | 2/2003 | Alshuler et al. | 606/9 |
| 6,595,986 B1 * | 7/2003 | Almeida | 606/9 |

* cited by examiner

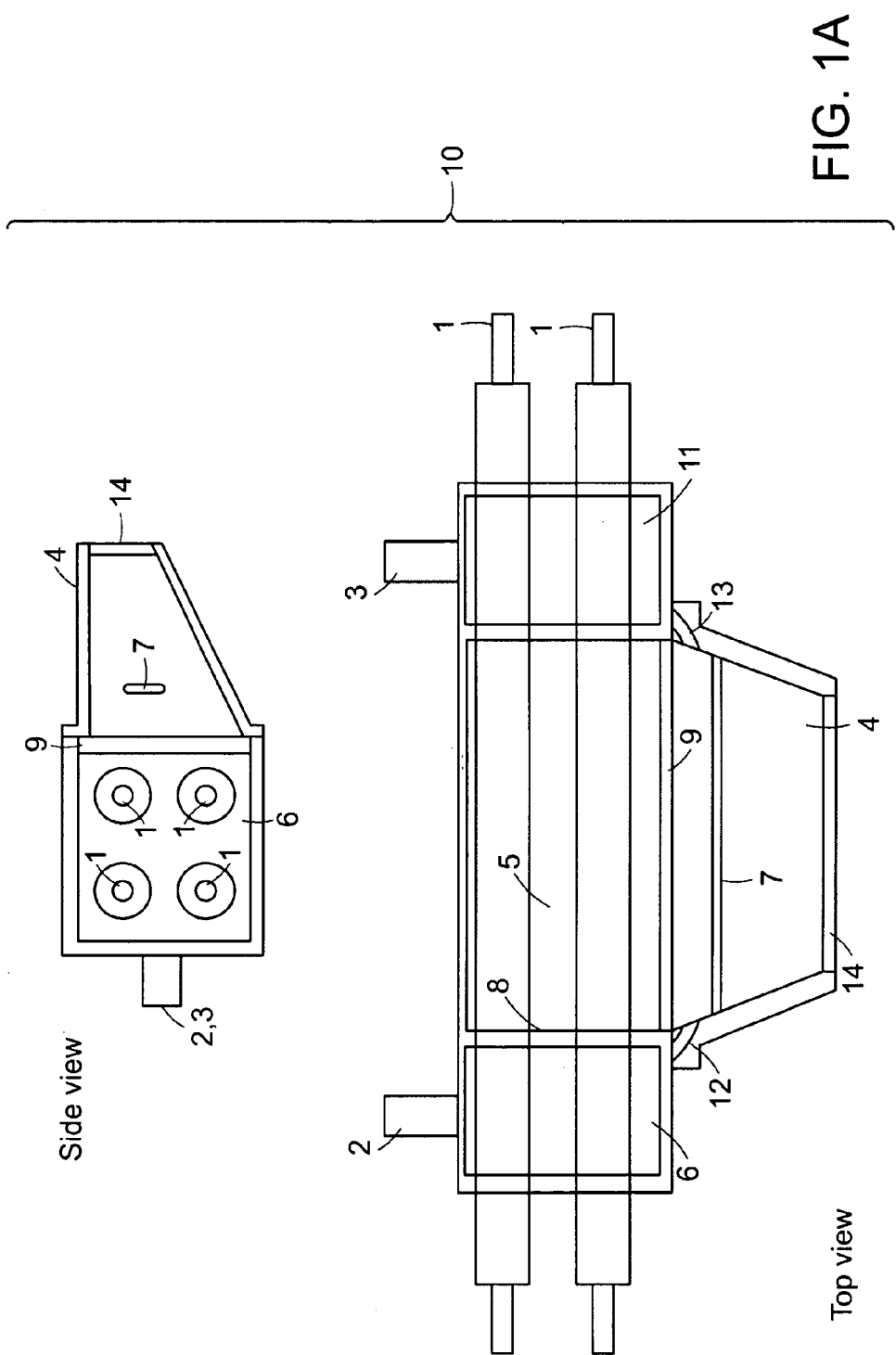

DUAL FILTER MULTIPLE PULSE PHOTO-DERMATOLOGICAL DEVICE WITH PRE/POST OPTICAL HEATING, QUASI-LOGARITHMIC SPACING, AND LASER ROD SPECTRUM INFUSION

CROSS REFERENCE TO RELATED APPLICATIONS

This application is a continuation-in-part of the U.S. patent application Ser. No. 09/841,816 filed Apr. 25, 2001, now U.S. Pat. No. 6,595,986 which is a continuation-in-part of U.S. patent application Ser. No. 09/173,422 filed on Oct. 15, 1998, which is now U.S. Pat. No. 6,228,074 issued on May 8, 2001, which is incorporated herein by reference in its entirety.

BACKGROUND OF THE INVENTION

This invention relates to a method and device for treating and removing various skin conditions and lesions using flashlamps. There exists a multitude of common skin problem which can be caused by many reasons. Conditions such as excessive hair, age spots, freckles, superficial veins, wrinkles, acne, rosacea and collagen shrinkage due to old age to name just a few. There are many products and methods for treating such skin conditions. The methods can include one or a combination of external creams, chemicals, internal medications, laser devices, mechanical devices, and surgery.

These methods vary in effectiveness, pain, term of benefit, side effects, duration of treatment, and cost of procedure. Unfortunately, to treat all the various skin conditions generally requires multiple devices and/or treatment modalities. Because of this need for multiple devices and modalities to treat numerous skin conditions, a single device that could treat a great number of skin conditions would make treatments more accessible to the public.

Prior art methods such as Altshuler et al. U.S. Pat. No. 6,511,475 utilizes continuous wave light as apposed to a pulsed light system. The Altshuler device does not create high peak temperatures in a short time span due to its continuous wave nature. This inability to create high peak temperatures in a short time span prohibits its use in a wide variety of skin conditions.

While another prior art method disclosed in Eckhouse et al. U.S. Pat. No. 6,514,243 utilizes pulsed light. Its particular spectrum distribution pattern requires the use of a cooling gel to prevent discomfort to the patient. Unfortunately, the spectrum distribution pattern of the Eckhouse device may cause damage to the treatment area skin. Further, the lack of multiple lamps severely limit the range of skin conditions that the Eckhouse device is able to treat.

SUMMARY OF INVENTION

The present invention provides a method in which a variety of unwanted dermatological conditions can be removed or treated without damage to the skin. The device emits a multi-wavelength spectrum which is absorbed in many chromophores such as melanin, blood, certain tissue structures, and certain bacteria. Since the inventive device emits a multi-wavelength spectrum that is absorbed by many chromophores, the device can treat the following dermatologic conditions such as but not limited to the following: blood vessels, pigmented lesions, acne, Rosacea, wrinkles, hair removal, photo-modulation, collagen rejuvenation, and skin smoothing.

One illustrative embodiment of the inventive device allows the removal of superficial blood vessels from selected areas of the skin in an efficient and painless manner. According to the invention, the method of blood vessel removal consists of delivering a specific pattern of non-laser generated multiple light wavelengths which pass through the skin and into the blood vessel. The absorption of these various wavelengths results in thermal and photochemical damage to the selected vessel and its components. The multiple wavelengths that are utilized in this treatment occur at different intensities throughout the wavelength spectrum of about 400 nm to about 1200 nm producing a pattern that achieves optimal depth penetration.

The multiple wavelength spectrum, according to the invention, is produced by four flashlamps consisting of a specific mixture of krypton and xenon gas encased by a cerium oxide doped synthetically fused quartz envelope. The four flashlamps are connected to separate user intensity controlled power supplies that are specifically designed to produce approximately a 14 ms pulse duration with a specific pulse discharge pattern to accommodate different size dermatologic targets. Electrical supply energies of 160–400 joules are input to the flashlamps per $cm^2$ of output. It is contemplated within the scope of the invention that the electrical supply energy can be generated with typical household or commercial current or can be generated by the use of battery power.

Each flashlamp can be fired simultaneously, with an overlap, or with a time duration of up to about 40 ms between each pulse. The spacing between each pulse grows consecutively larger to regulate tissue temperature avoiding unwanted tissue damage. This spacing technique eliminates the need for epidermal cooling and topical anesthetics preventing injury and pain to the patient.

The four flashlamps form a pulse train of four individual pulses which results in a treatment shot. Each treatment shot is separated by approximately 3 second intervals to allow the user to move the delivery system to another area of the body for subsequent treatment. The pulse length and characteristic shape of each individual pulse is designed to distribute the energy over a period of time that substantially eliminates damage to the skin that can occur in prior art methods.

The inventive device allows adjustment to the intensity of the light source and delay between each individual pulse. The adjustment of the intensity and delay of the light source allows the user to adjust the treatment shot to accommodate different skin and dermatologic target types.

The flashlamps utilized in the inventive device are housed in a polyester head. It is contemplated within the scope of the invention that the flashlamp housing may be fabricated from materials known in the art. The flashlamp head is connected to a hollow internally reflective rectangular light guide by means of a 400 nm high pass filter. There exists a clear window on the rim of the light guide to stop plume from the skin from contaminating the reflector. The light guide is pressed against the skin forming an optical seal. The non-collimated light, consisting of wavelengths greater than about 400 nm, passes through the 400 nm high pass filter and reflects at infinite angles down the hollow light guide into the skin reaching the skin, tissue, and dermatological targets.

In an alternative illustrative embodiment of the inventive device, modification to the output wavelength pattern of the apparatus, by the use of a different light filter, allows the apparatus to be effective in destroying particular dermatological targets and lesions.

BRIEF DESCRIPTION OF THE DRAWINGS

The foregoing and other features and advantages of the present invention will be more fully understood from the following detailed description of illustrative embodiments, taken in conjunction with the accompanying drawings in which.

DETAILED DESCRIPTION

Figure 1B:
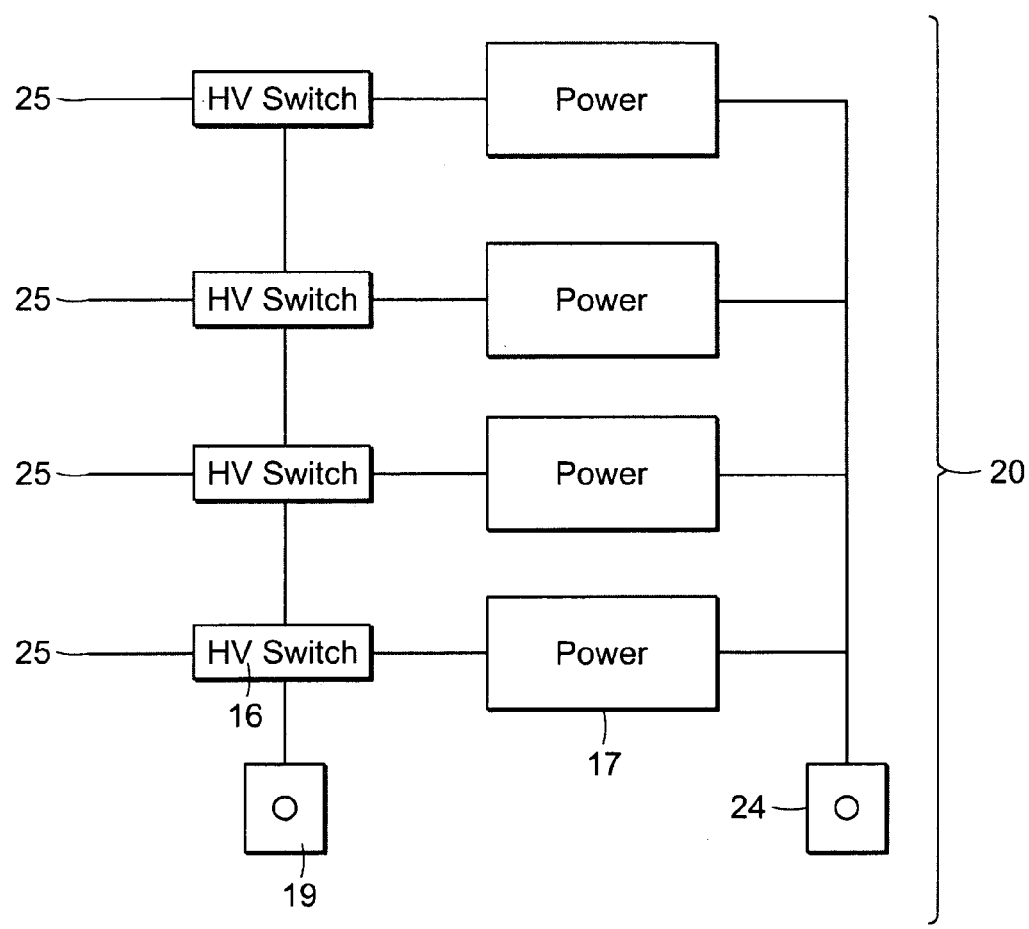
FIG. 1 is a cross sectional view of the delivery head of the device which generates and delivers the multiple wavelengths to the hair and its components and a block diagram of the power supplies and controlling electronics which control the lamps in the delivery head.

Referring in detail to the drawings, a flashlamp apparatus, according to the present invention is shown in FIG. 1. The water cooled delivery head 10 containing multiple flashlamps 1 each having an individual power source capable of timed firing 20 that creates the light output for dermatologic treatment which exits through the light guide window 14. The multiple flashlamps 1 each contain a combination of approximately 90% krypton gas and 10% xenon gas. This gas combination creates a specific spectral distribution pattern.

The container material of the flashlamps 1 is comprised of synthetic quartz to eliminate impurities. The use of synthetic quartz prevents the degradation of the flashlamps 1 after prolonged use. Additionally, the synthetic quartz is doped with cerium oxide in order to block ultraviolet light under 390 nm from the lamp and thereby maintaining the integrity of a reflective chamber 5 and high pass filters 7, 9. The cerium doping also has the ability to convert ultraviolet light, which would normally become waste heat, into higher wavelengths which can pass through the high pass filters 7, 9 to create a more efficient conversion of electrical energy to light output.

The reflective chamber 5 is made of a metallic or ceramic material whose reflectivity coincides with the desired output of wavelengths greater than high pass filters 7, 9. In one illustrative embodiment gold is used to construct the reflective chamber 5. Gold reflects over 95% of light at about 610 nm and higher wavelengths while reflecting approximately 60% of light at lower wavelengths. In performing hair removal, the desired wavelength output is greater than about 610 nm. The reflectivity of gold partially absorbs the lower wavelengths in the reflective chamber 5 so the high pass filter 9 does not bear the full absorption of the lower wavelengths which may result in damage to the high pass filter 9. Other reflective materials that are well known in the art can be used to construct the reflective chamber 5 these materials include, but are not limited to brass, copper, plastic, and ceramic or the like.

In an alternative illustrative embodiment a full spectrum reflectant ceramic is used in the reflective chamber 5 and light guide 4. By using two filters 7, 9 with long pass filters 610 nm and 495 nm respectively, a spectral distribution pattern can be constructed to be effective on multiple dermatologic modalities. The delivery head 10 is cooled by water which flows in through an inlet port 2 and fills a first chamber 6, the water then flows over the flashlamps 1 into the reflective chamber 5 and simultaneously in lightguide 4 by way of water channel 12. The water then flows into chamber 11 by way of reflective chamber 5 and water channel 13. Once the water enters chamber 11, it then exits out of delivery head 10 through an outlet port 3. The water, which flows through the delivery head 10, is recycled in a closed cooling system having a radiator and fan assembly, which uses room air as the heat exchange. The cooling system should maintain water temperatures surrounding the flashlamps 1 below a maximum continuous operating temperature of about 100 degrees Celsius. Since the electrodes of flashlamps 1 create the greatest heat, chambers 6 and 11 allow a greater volume of water and thus thermal exchange over these areas.

One illustrative embodiment of the present invention uses an optically transparent epoxy coating 8 to coat the metallic reflector preventing oxidation and degradation from the water cooling that flows through the delivery head 10. The water is used solely to cool the lamps 1, reflective chamber 5, long pass filters 7, 9, and light guide 4. The water is kept in the system by light guide window 14 which is used sealed to the light guide 4.

The warm water cooling does not cool the skin at light guide window 14. The pulse shape, pulse length, and quasi-logarithmic pulse spacing, further explained in FIGS. 4, 5, 6 eliminate the need for skin cooling. Another illustrative embodiment utilizes high volume forced air instead of water to cool the delivery head 10. This embodiment severely sacrifices repetition rate of firing and total power output capabilities but may be used in a low power portable device. It is contemplated within the scope of this invention that the forced air may be cooled prior to introduction to the delivery head to improve the removal of heat.

The commercially available high pass filters 7, 9 known to those skilled in the art transmits only wavelengths above their set value. A typical 400 nm high pass filter can be use includes but is not limited to a CVI LASER (Model# GCG-GG-400-1.00) In one illustrative embodiment of the invention, 400 nm and 630 nm high pass filters 7, 9 are used. Any wavelengths that pass through the filters 7, 9 below the filter value are absorbed and converted to heat. The cooling water in the reflective chamber 5 and light guide 4 are also in contact with high pass filters 7, 9 extracting heat due to the lower wavelength absorption. The high pass filters 7, 9 only allows wavelengths above 400 nm and 630 nm respectively to enter into the hollow reflective light guide 4.

A power source and firing apparatus 20 are connected to the delivery head 10. The flashlamps 1 are connected to high voltage switches 25. Each flashlamp 1 is connected to its own power supply 17 via the high voltage switches 16. Each power supply 17 supplies approximately 40 to 100 joules of electrical energy to each flashlamp 1 of every $cm^2$ of output. A firing sequence control 19 is used to activate a trigger 16 for each flashlamp 1 in a simultaneous or consecutive order. An output intensity control 24 regulates the electrical energy of the individual power supplies 17, which discharge through the flashlamps 1. The firing sequence control 19 regulates the amount of time it takes for the output energy of one treatment shot to be dispersed while the output intensity control 24 regulates the amount of energy delivered.

In one illustrative embodiment a single lamp 1 is connected to each high voltage switch 25. This system switches each power supply 17 to the same lamp. This embodiment can only be used for consecutive firing and lower power due to the single lamp limitations.

Figure 2:
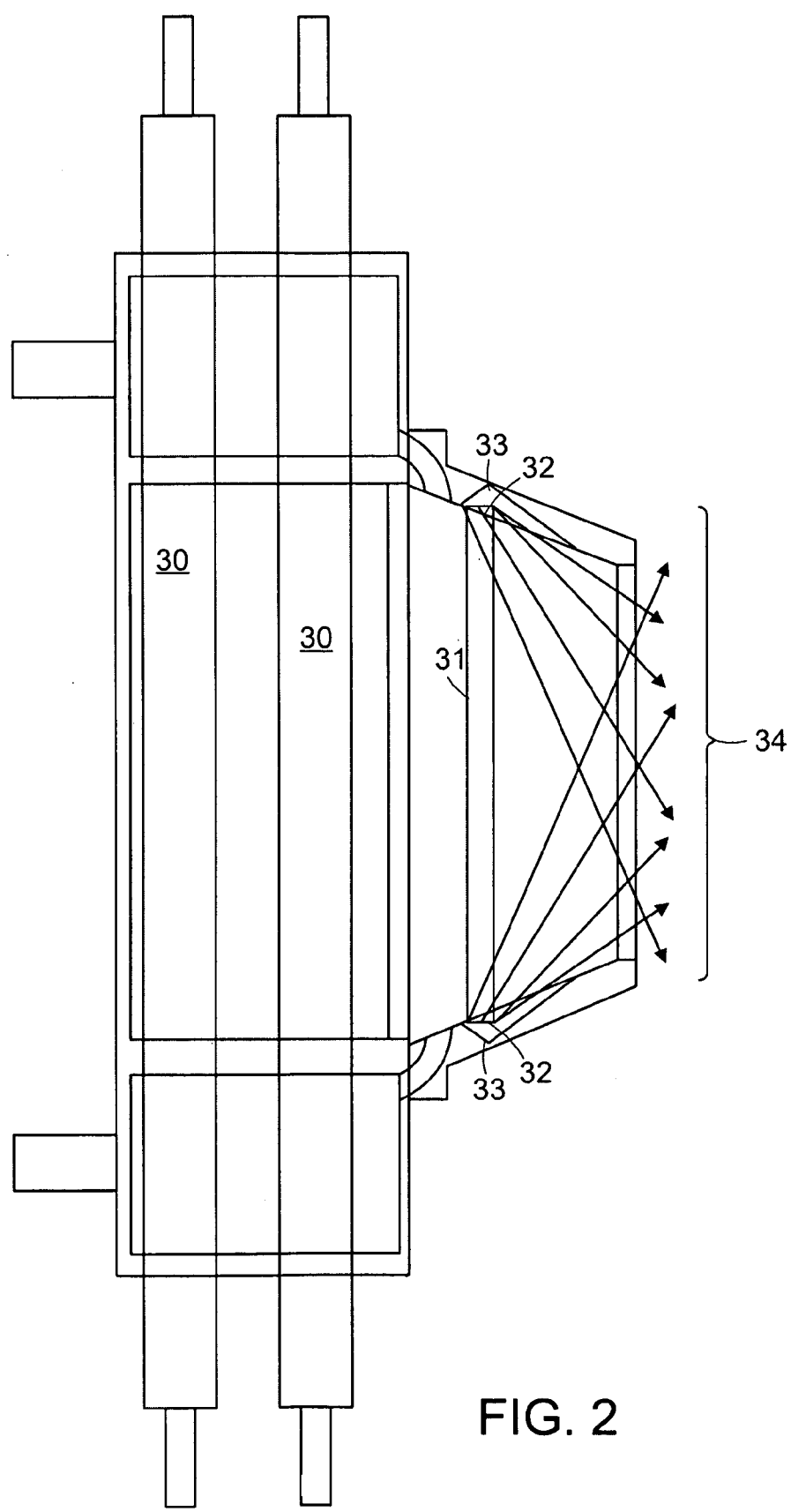
FIG. 2 is a cross sectional view of the delivery head with apparatus for laser rod spiking of output wavelength.

Referring to FIG. 2 a cross sectional view of the delivery head with laser rod spectrum spiking is shown. In one embodiment of the invention, a laser rod 31 is inserted in the light guide. The laser rod 31 is coated on both sides with a 75% reflective coating 32. The wavelength of the reflective coating 32 will be matched to the wavelength of the laser rod 31 chosen for spectrum spiking (e.g. Nd:YAG laser rod 31 emits a wavelength of 1064 nm, so the reflective coating 32 must match this wavelength for function). When the device is fired, the lamps 30 excite the laser rod 31 and create laser action by photons reflecting back and forth between the 75% reflective coatings 32. Since the coating 32 is 75% reflectant, the laser rod 31 will emit single wavelength laser light at both ends of the laser rod 31 entering into the reflective chambers 33. The reflective chambers 33 will be geometrically designed to reflect the laser output forward through the light guide 34.

In one embodiment of the invention, the reflective chamber 33 will be formed out of a diffuse reflecting ceramic. This will provide homogeneous distribution of photons at the light guide exit 34. Since the lamps of the device 30 emit multi-wavelength light, many different absorbing types of laser rods 31 may be inserted into the device to choose the desired single wavelength spiking.

Figure 3:
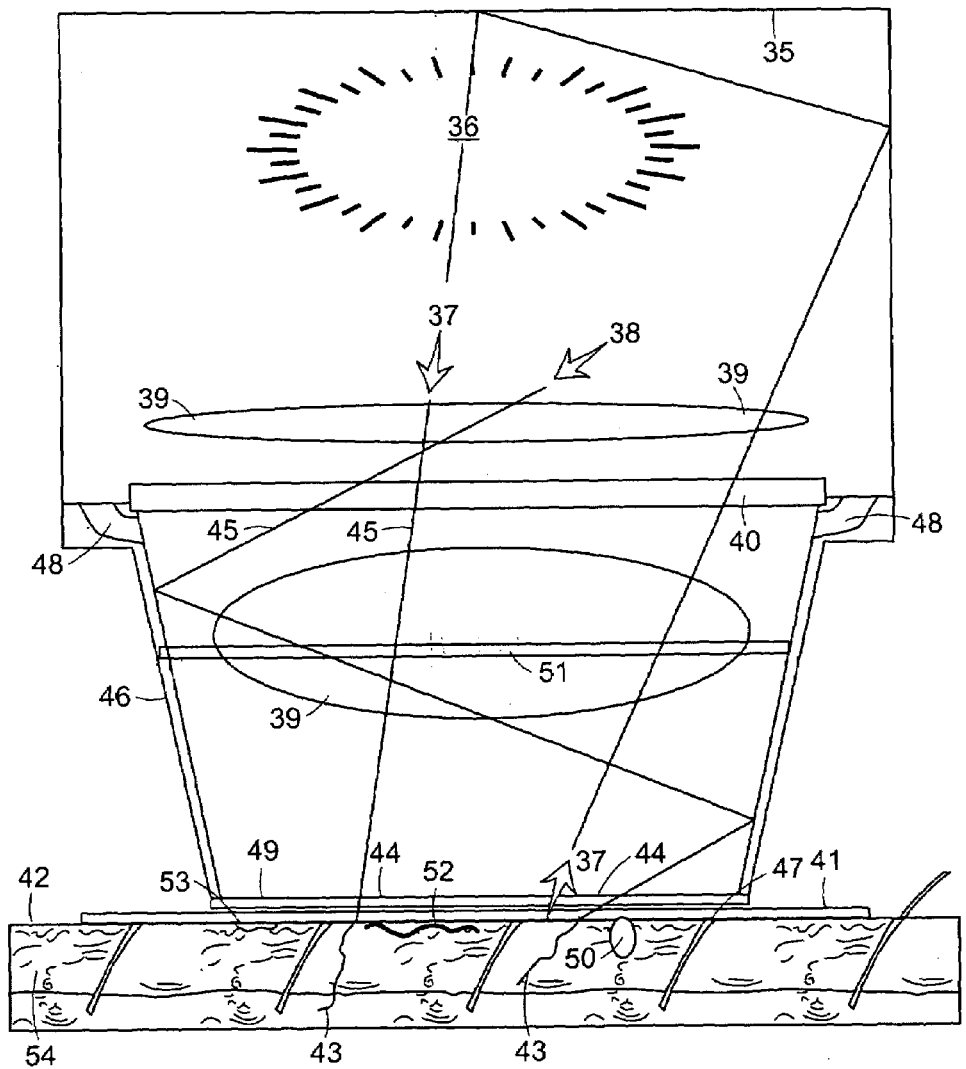
FIG. 3 shows the cross sectional view of the delivery head and light guide with conceptual function.

Referring to FIG. 3 a cross sectional view of an alternative delivery head is shown. The light source from the flashlamps 36 passes through the flashlamp cooling water 39 and is represented here by individual photons 38. Water coolant 39 is used to extract heat from the lamp light source 36 which flows into reflective chamber 35, through water channel 48, into light guide 46, and back into reflective chamber 35. Since the light source 36 is non-laser, and radially emitted, the photons 38 are reflected from the reflective chamber 38 and exit through the high pass filter 40 (assuming the wavelength is higher than the filters cutoff wavelength), at multiple angles 45, through the light guide cooling water 39, down the reflective light guide 46, through the second high pass filter 51 for further desired wavelength cutoff, through light guide window 49, then through a plume barrier lotion, and into the skin 54 at multiple angles 44 reaching various dermatological sights such as pigmented lesions 53, vascular lesions 52, acne 50, and the hair and its components 47 after scattering through the skin 43. Light that is reflected back from the skin 37 enters back into the light guide 46 and reflective chamber 35. Since the chamber and light guide are highly reflective, the photons that reflect off of the skin 37 will be re-directed back to the skin 37 and re-used for more efficiency.

The plume barrier lotion 41 is a transparent non-cooling lotion preventing plume from the heated skin and lesions from carbonizing and sticking to the light guide window 49. The hollow reflective light guide 46 is made of a non corrosive metallic or ceramic highly reflective material. The light guide window 49 is pressed against the skin 42 forming an optical seal preventing the escape of light outside the light guide. The light guide window 49 prevents plume from the heated skin and lesions from entering into and contaminating the reflective light guide 46. This optical seal ensures all energy is transmitted through the skin and into the skin and dermatological targets. Any hair is trimmed or shaved 47 prior to treatment so as to have no hair above the outer layer of skin that would absorb the light and block its transmission into the skin.

Figure 4A:
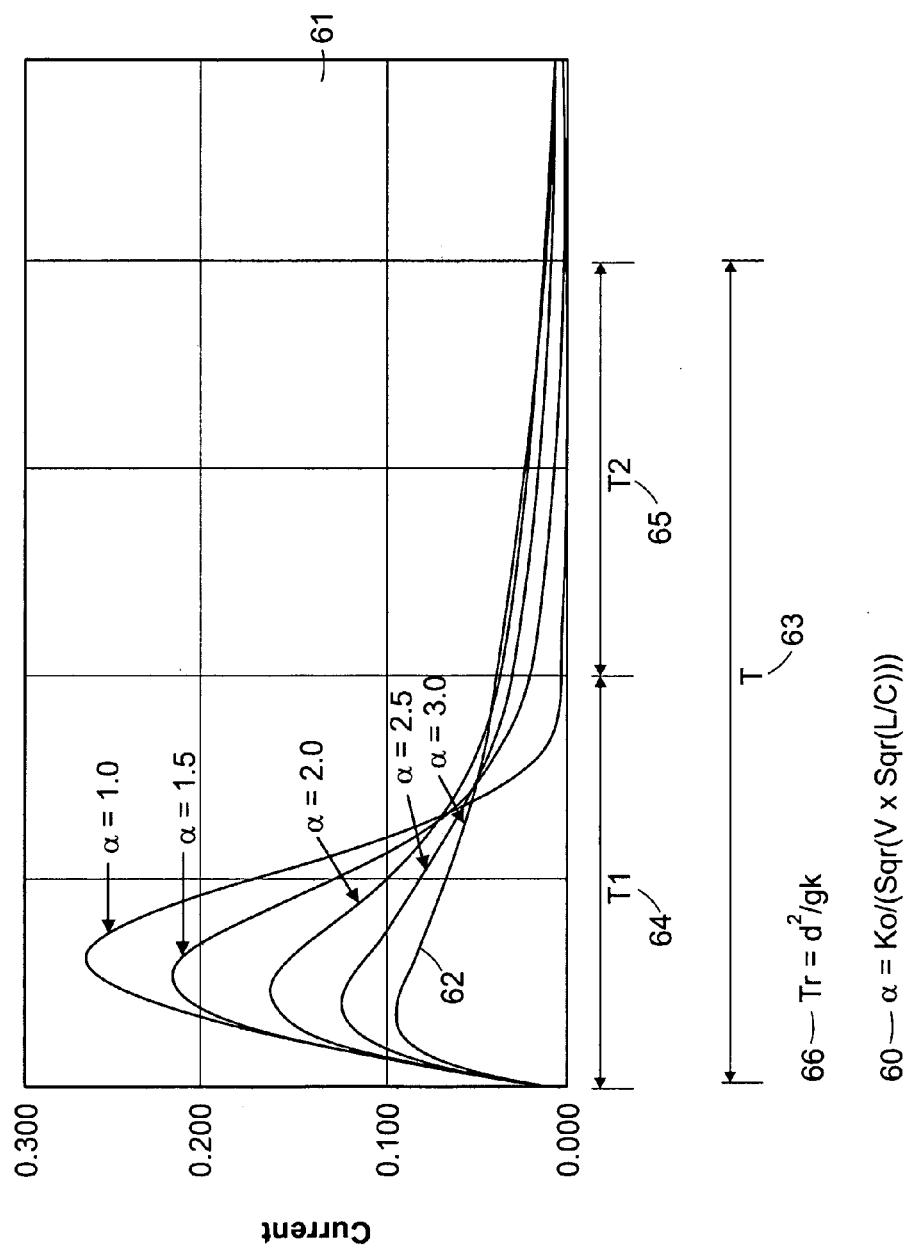
FIG. 4A shows the manipulated pulse geometry of the invention.

Turning now to FIG. 4A, a graphic representation of the pulse geometry and the pulse train sequence of the instant invention is shown. FIG. 4A shows the formula for damping factors 60 that create various pulse geometries 61 shown in the graph. The desired pulse geometry that provides the most efficacious results for destruction and treatment of dermatological lesions is a damping factor of three (3), which provides an elongated pulse 62. This pulse geometry takes advantage of the difference in thermal relaxation times of skin lesions and skin.

Thermal relaxation time is the time it takes for a body of particular size, shape, and material to dissipate 50% of its heat energy. The physical law is represented by equation 66 where d is the diameter of the body, g is the geometric factor, and k is the thermal diffusivity factor of the material. This specific pulse geometry as depicted in FIG. 4a, spreads the energy more evenly throughout the pulse length T 63 which is approximately 14 ms for the device. Since the thermal relaxation time of skin is approximately 10 ms, having the pulse duration over about 10 ms prevents damage to the skin by allowing treated skin to dissipate energy and thereby avoiding damaging high temperatures. Although a 14 ms individual pulse duration is used on the application device, it is contemplated within the scope of the invention that any pulse duration between 10 ms and 60 ms would provide a similar effect.

A further advantage of the pulse geometry according to the invention is to take advantage of various size dermatological lesions and components. Since dermatological lesion sizes vary in any particular area of the body, so do their corresponding thermal relaxation times. The optimum pulse duration and geometry would be one that can be effective on the broad size dermatological lesions while sparing damage to the surrounding tissue. The average size dermatological lesion will vary in thermal relaxation times from 10 ms to 150 ms. By using this specific pulse geometry, optimum damage is confined to the dermatological lesion for large and small sizes. Small lesions having a thermal relaxation time of 20 ms would dissipate the heat into the surrounding tissue rapidly resulting in a lower peak temperature in the hair follicle and creating high temperatures in the tissue. By using this specific pulse geometry 62, greater then 70% of the energy is delivered in the first half of the pulse T1 64 while the remaining energy is dispersed in the second half of the pulse T2 65. This still allows adequate cooling time for the skin but creates higher temperatures in the small lesions since most of the energy is delivered in a short amount of time not allowing the lesion time to disperse the energy to the surrounding tissue. Large lesions having higher thermal relaxation times up to 150 ms are also affected since even more time is required to disperse the energy.

Figure 4B:
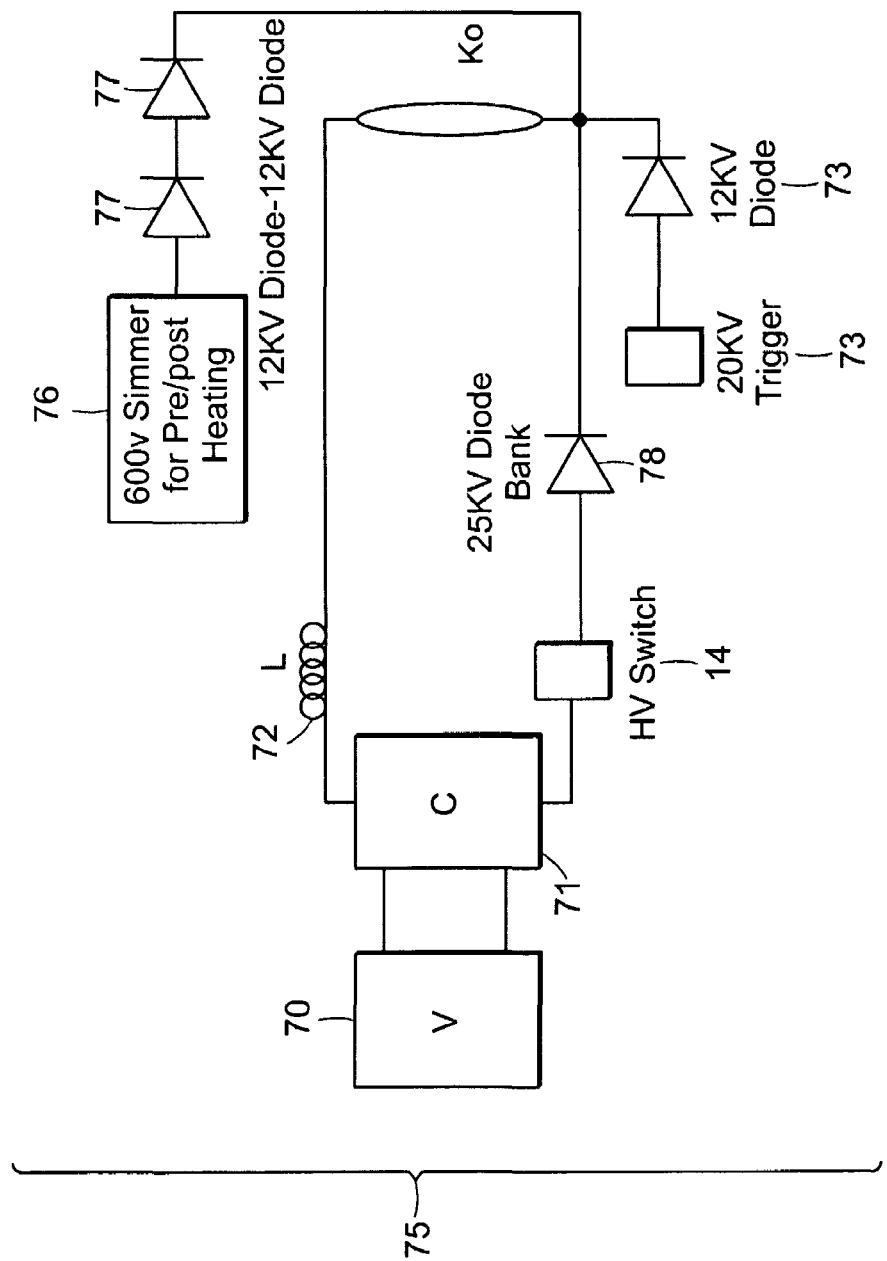
FIG. 4B shows basic circuit components to form pulse geometry and create optical pre/post heating of dermatological targets.

Referring to FIG. 4B, a schematic of the flashlamp circuit 75 necessary to accomplish desired pulse geometries pre/post lesion heating is shown. A high voltage spike is generated by a trigger transformer circuit 73. The trigger circuit 73 ionizes a flashlamp 79 so that a 600V simmer circuit 76 keeps the flashlamp 79 continuously illuminated at a low level. A voltage supply 70 charges a capacitor 71. When a high voltage switch 74 is activated, a capacitor 71 discharges through a diode bank 78 and an inductor 72 into the flashlamp 79. The flashlamp has a certain resistance known as Ko. The values of the components in the circuit 75 must provide a damping factor of three (3) when inserted into formula 60 and also provide a pulse duration T, as shown in FIG. 4A, 63 of 14 ms.

Figure 5A:
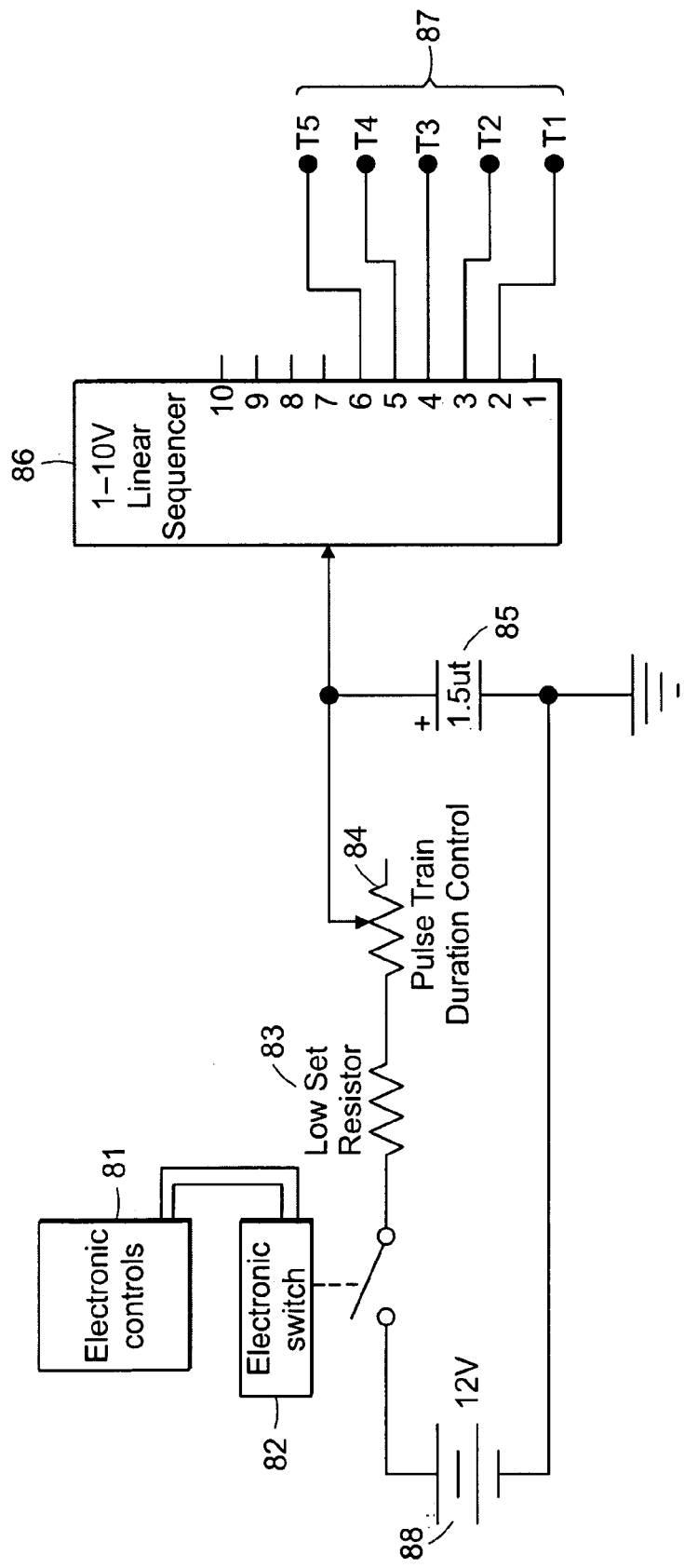
FIG. 5A shows the basic circuitry to create the quasi-logarithmic pulse spacing according to the invention.

Referring to FIG. 5A a circuit that generates quasi-logarithmic pulse spacing is shown. The circuit is powered by a 12DC power supply 88. To start the triggering sequence of the flashlamps used in the invention, electronic controls 81 send a signal out to a solid state electronic switch 82 commencing the sequence. When the electronic switch 82 is closed, a capacitor 85 is charged through a low set resistor 83 and a duration control resistor knob 84. These resistors 83, 84 control the charge rate of the capacitor 85. The low set resistor 83 sets the minimum charge rate when the pulse train duration knob 84 is set to the minimum value. The 1 to 10V linear sequencer 86 is a voltage bar graph meter that increases 1 step for every 1 volt 87 detected on the capacitor 85. Since the capacitor 85 charges at a logarithmic rate, there will be an increase in time between each 1V step. When the sequenced output T1–T5 87 is used to trigger each flashlamp, there is also an increase of time between the firing of each flashlamp. This timing technique creates the quasi-logarithmic pulse spacing.

Figure 5B:
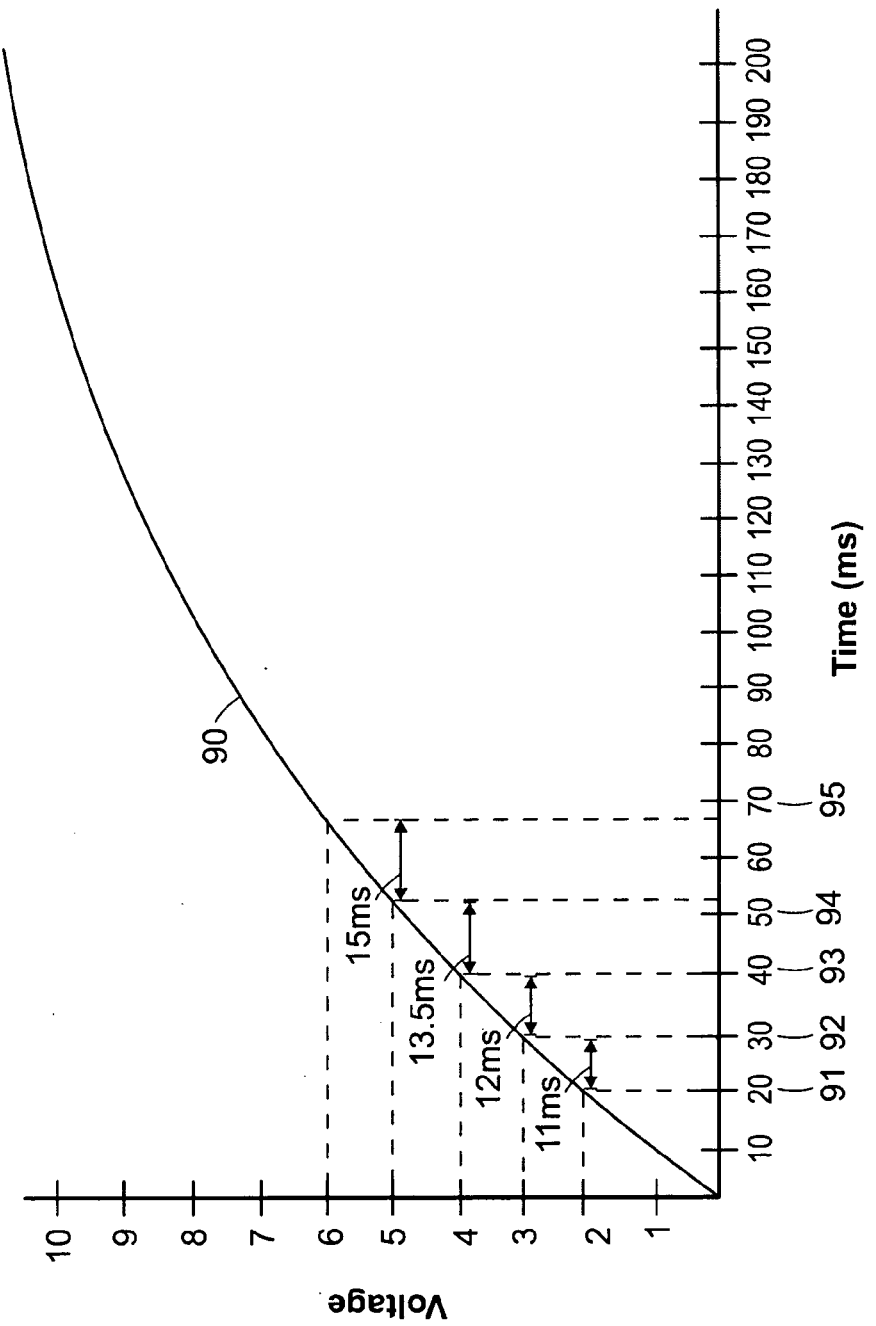
FIG. 5B shows a steep logarithmic charge curve which creates short quasi-logarithmic spacing according to the invention.

Referring to FIGS. 5A and 5B, the charge curve 90 of the quasi-logarithmic circuit capacitor 85 is shown. The voltages on the Y axis of the graph from 2 to 6 volts corresponds to the 1–10v linear sequencer output 86 Fig. The timing in (ms) indicated on the X axis of FIG. 5B 91, 92, 93, 94, 95 as it corresponds with the charge curve 90, indicates the spacing between each flashlamp pulse when the duration control 84 is set to a certain setting.

Figure 5C:
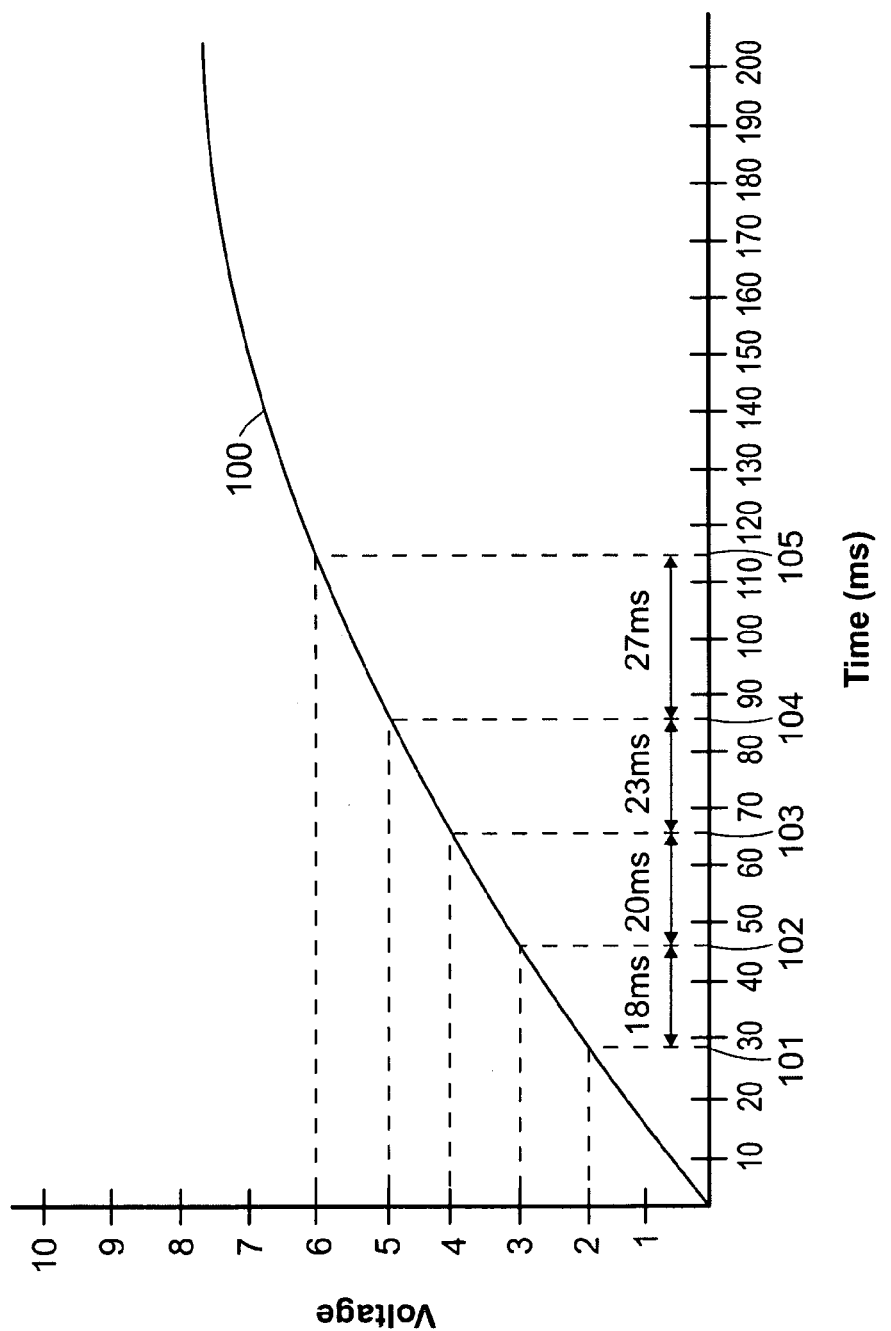
FIG. 5C shows a shallow logarithmic charge curve which creates long quasi-logarithmic spacing according to the invention.

FIG. 5C depicts the spacing 101, 102, 103, 104, 105 between each flashlamp pulse when the duration control 84 FIG. 5A is set to a higher setting than that shown in FIG. 5B. A higher setting of the duration control 84 as depicted in FIG. 5A, will create a shallower charge curve 100 than a lower duration control 84 setting curve 90 FIG. 5B.

Figure 5D:
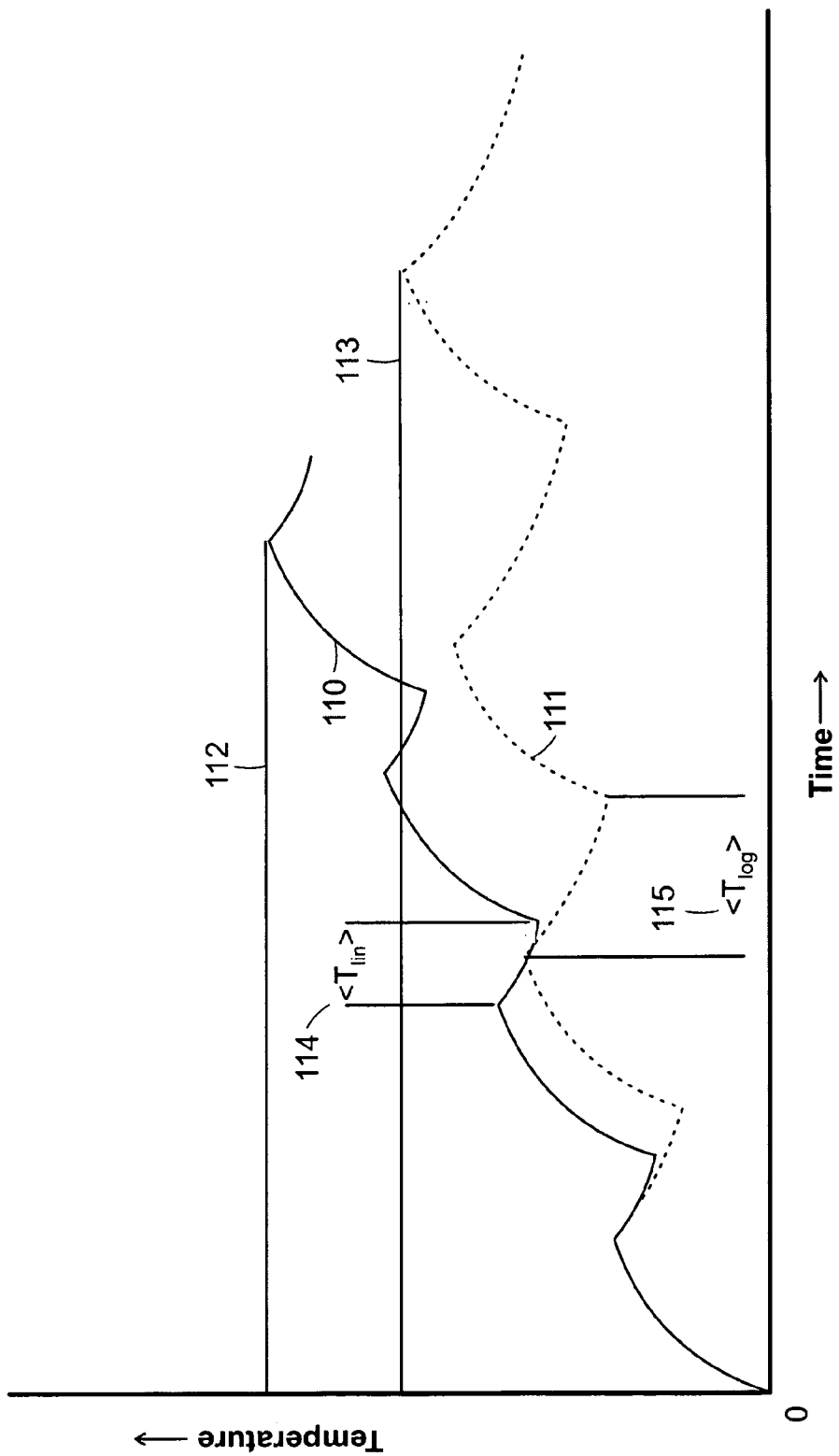
FIG. 5D shows how quasi-logarithmic spacing reduces peak temperatures as compared to linear spacing.

FIG. 5D shows the temperature effect on tissue from quasi-logarithmic spacing. The tissue temperature for normal linear spacing is depicted in curve 110. With linear spacing, the time between each pulse 114 is equal. With quasi-logarithmic spacing, the tissue temperature is depicted in curve 111. The spacing between each pulse 115 in quasi-logarithmic spacing is greater with each consecutive pulse. The peak temperature in tissue for linear spacing 112 is higher than that with quasi-logarithmic spacing 113. Since the tissue has a greater time between each pulse 115, more time is allowed to conduct heat to surrounding tissue and lower the peak temperature. This lower peak temperature 113 decreases the risk of scarring and skin damage.

Figure 6A:
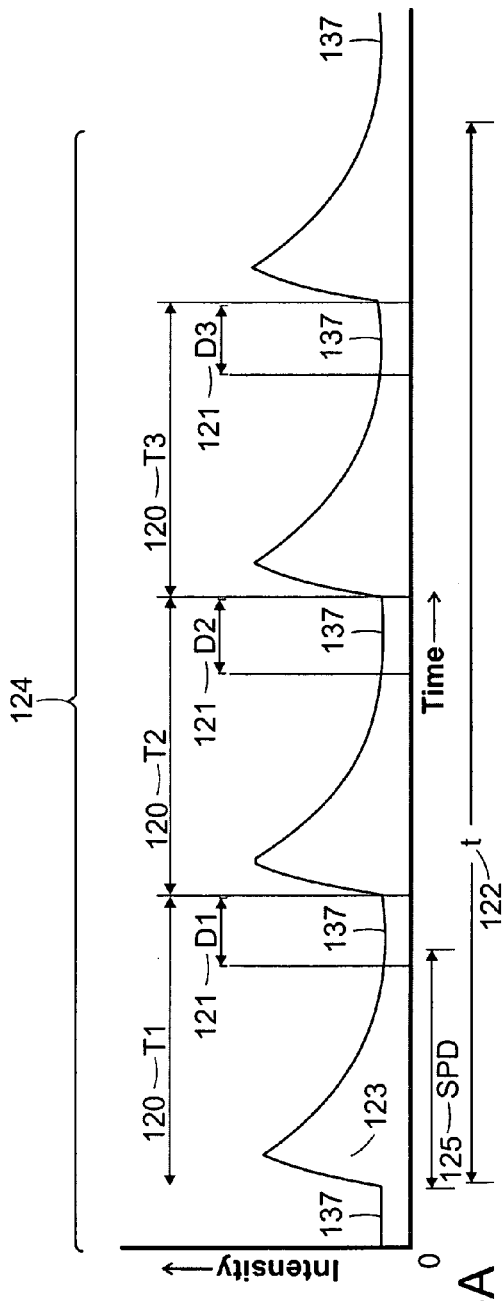
FIG. 6a shows the quad pulse train of each treatment shot and the controlled delay between each pulse.

Referring to FIG. 6A, a treatment shot is shown according to the invention when the treatment shot is set for consecutive firing with delays between each pulse 124. The treatment shot consists of a four-pulse sequence train with a time delay between each pulse 121. A single pulse 123 is fired from the apparatus with a time delay of T 120 before the next consecutive pulse in the four-pulse train is triggered. If T 120 is greater than a single pulse duration (SPD) 125, which is approximately 14 ms, then a delay D 121 is created between each pulse. This delay 121 between each pulse allows the skin to cool before then next consecutive pulse is triggered. The total time it takes the apparatus to deliver the energy is T 122 which is the combination on all the delays 121 and all the SPDs 124. This time T 122 is the duration of the treatment shot. Each treatment shot is separated by a three-second interval to allow the user to move the delivery head to the next consecutive area for treatment.

One illustrative embodiment utilizes optical pre/post lesion heating. This optical pre/post heating consists of the flashlamps emitting a continuous low level light output 137 of the same wavelength characteristics as the single pulse output before and after each pulse. This low level output 137 is present between each pulse.

Figure 6B:
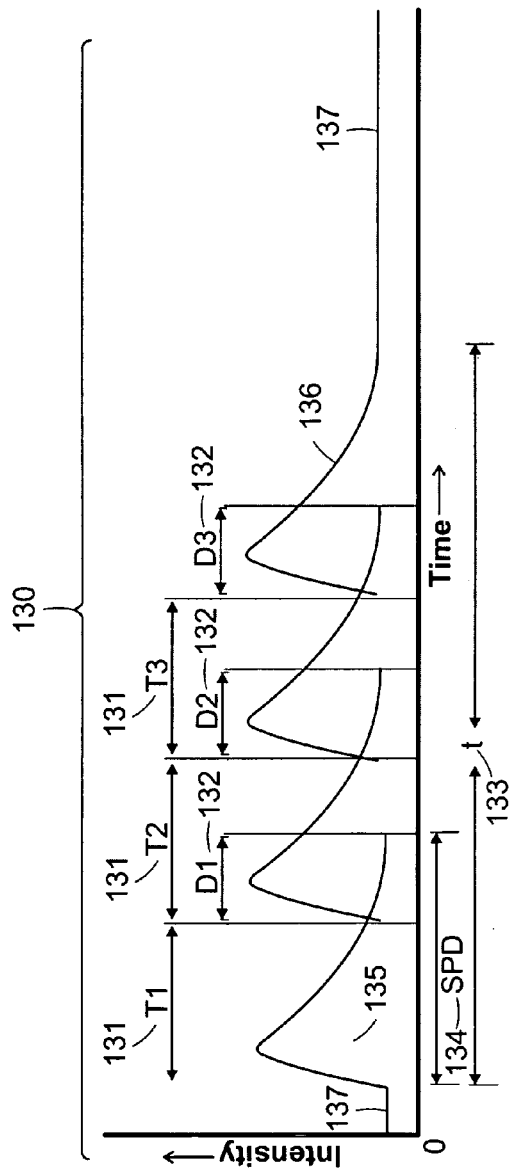
FIG. 6b shows the quad pulse train of each treatment shot with a negative delay that signifies overlap.

Referring to FIG. 6B that depicts a treatment shot from the apparatus when the treatment shot is set for overlap firing. The treatment shot consists of an overlap of single pulses in the four-pulse train 130. Since the flashlamps are connected to separate power supplies, the apparatus is capable of overlapping pulses. If a single pulse is fired from the apparatus 135 with a consecutive triggering time delay T 131 which is shorter than the SPD 134, then a negative delay (−) D 132 is created which represents an overlap of the consecutive pulses. This overlap transforms the four single pulses into a single sawtooth appearing pulse 136 of duration T 133. This single sawtooth pulse 136 allows more energy in a shorter amount of time T 133 than a single lamp system incapable of overlap. This higher energy in a shorter amount of time allows for more treatment options. The pre/post optical heating 137 is also an option with overlap firing of pulses.

Figure 7A:
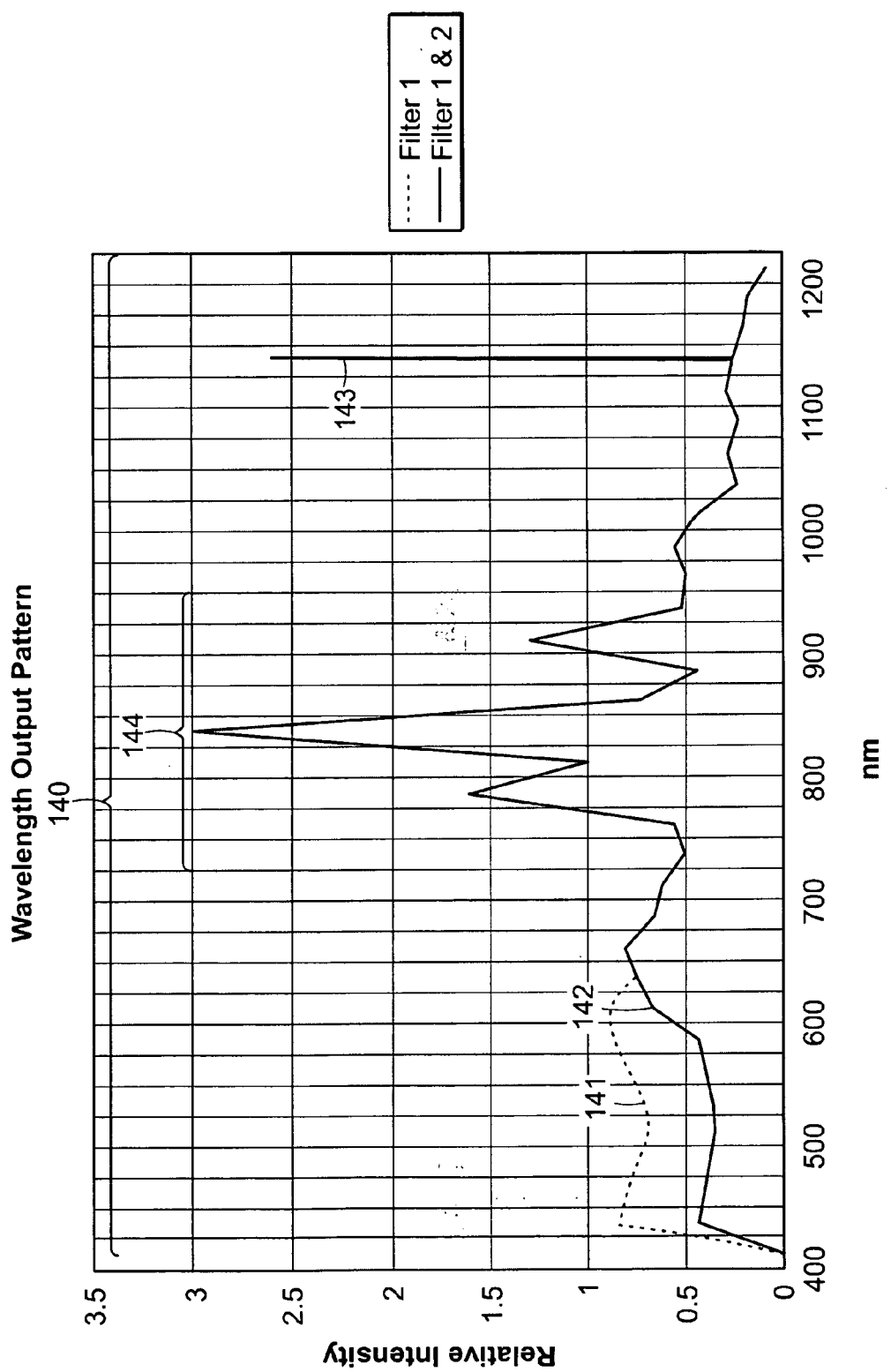
FIG. 7A is the relative intensity pattern of wavelengths generated by the invention.

Referring now to FIG. 7A, a spectral output pattern according to the invention is shown. The relative intensity spectral output distribution pattern 140 of the device is designed to simulate a bell curve throughout the useful spectrum of about 400 nm to about 1200 nm by creating central peaks of high intensity 144 while tapering off the lower and higher wavelengths 142. This spectral output distribution pattern creates an optimum output which benefits are explained in detail in FIG. 7E. The effect of the small second high pass filter as depicted in FIG. 1 is shown by the dotted wavelength cutoff section 141. Since this second small filter does not completely block the light entering the light guide, it only reduces the wavelengths below the cutoff value of the filter, not block them. The result of the dual filters is shown by a first curve 142. A second curve 141 is the wavelength output without the second filter. The benefit of the dual filters as shown in FIG. 1 is to further modify the spectral output pattern 140 to be useful on all types of dermatologic lesions without the need to change filters.

Figure 7B:
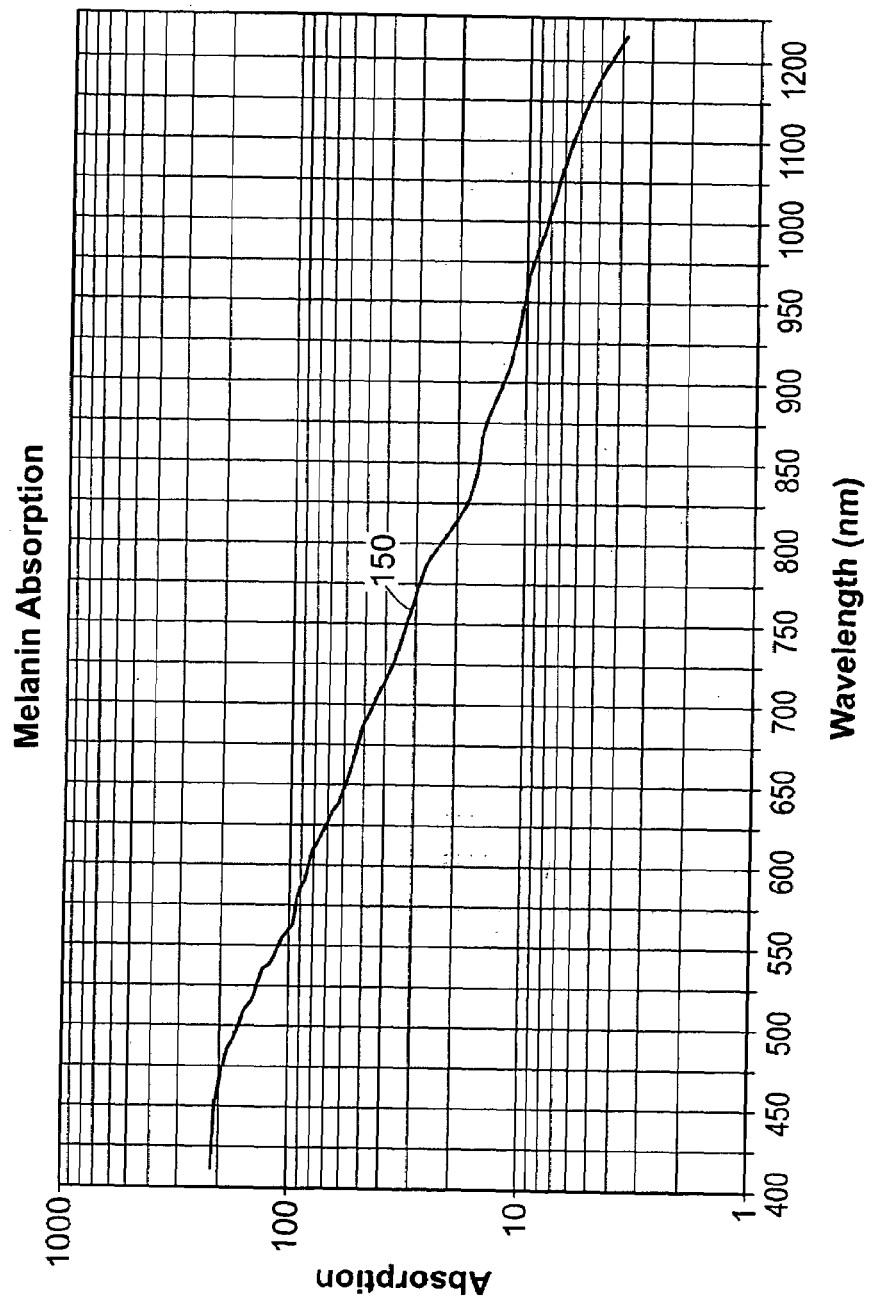
FIG. 7B shows melanin absorption throughout the spectrum region.

Referring to FIG. 7B which demonstrates the absorption of light in melanin throughout the wavelength spectrum. A logarithmic curve 150 shows how melanin absorption decreases as the wavelength increase. Since melanin is the absorbing chromophore in many dermatological targets, the logarithmic curve 150 demonstrates how more energy is necessary to heat up a target as the wavelength increases due to absorption factor. The reaction of the device output FIG. 7A as it corresponds to melanin absorption is shown in detail in FIG. 7E.

Figure 7C:
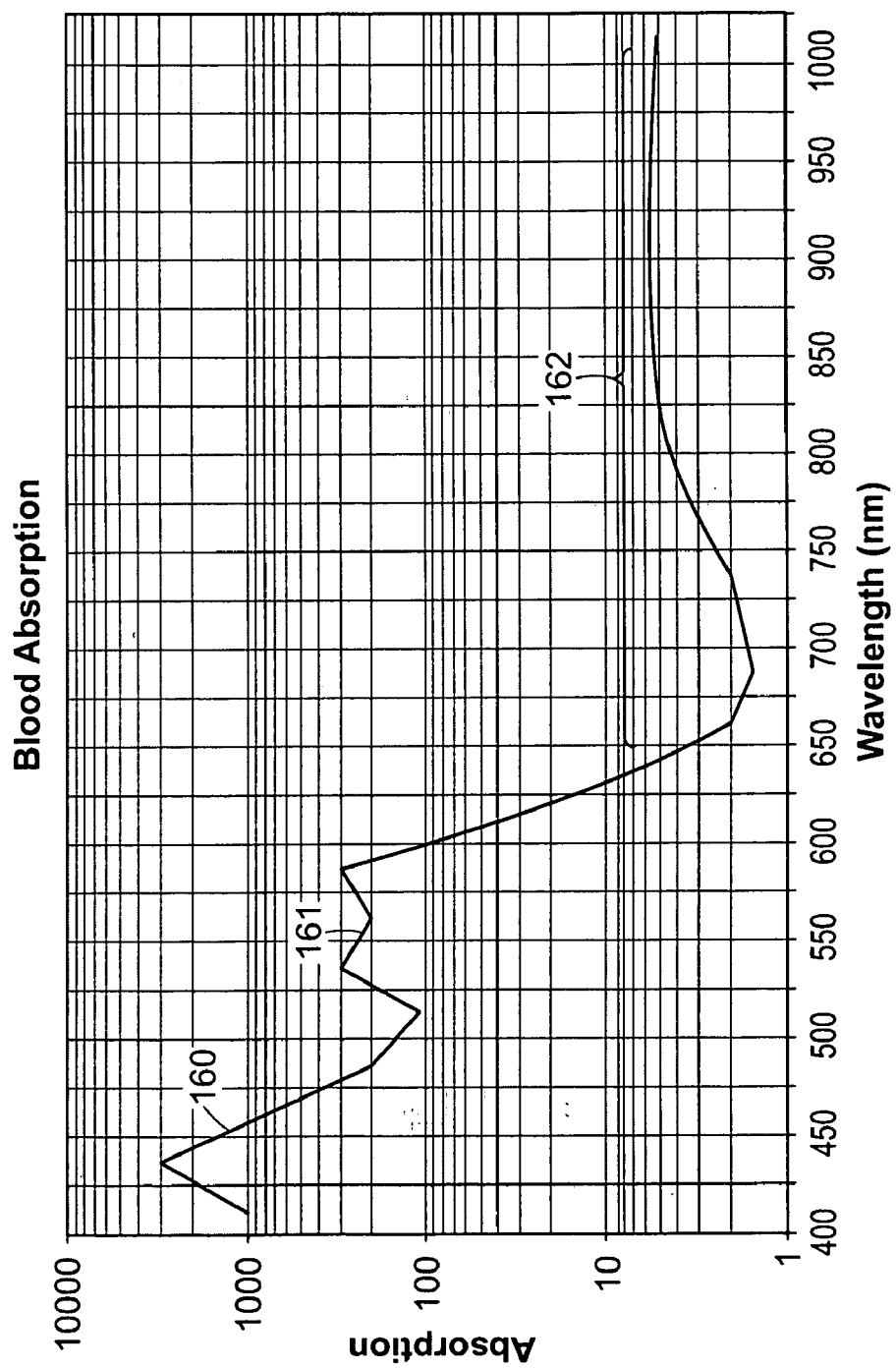
FIG. 7C shows blood absorption throughout the spectrum region.

Referring to FIG. 7C, the absorption of light in blood throughout the wavelength spectrum is depicted. Absorption of light by blood is very high from about 400 nm to about 475 nm 160 with a high peak of absorption from about 500 nm to about 600 nm 161. Wavelengths above 650 nm have very little absorption by blood. Blood is the absorbing chromophore for vein and angioma removal as well as stimulating collagen growth. Collagen growth is accomplished by heating blood and stimulating fibroblasts. This reaction also decreases wrinkles and smoothes the skin as a result. The graph shows how the lower wavelengths 160, 161 are necessary for blood based dermatological targets. The reaction of the device output FIG. 7A as it corresponds to blood absorption is shown in detail in FIG. 7E.

Figure 7D:
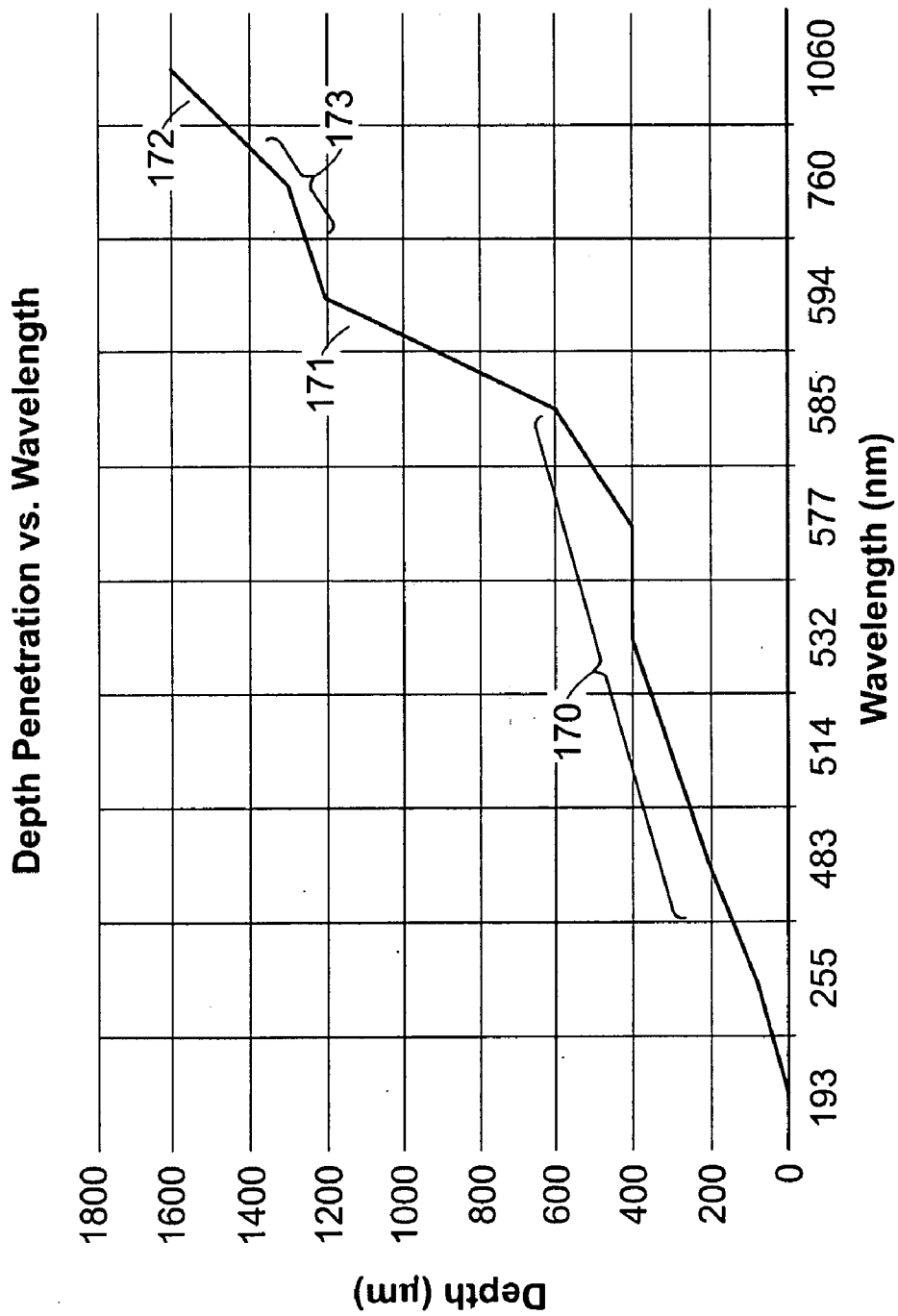
FIG. 7D shows depth penetration throughout the spectrum region.

Referring to FIG. 7D which graphically depicts the penetration depth of light versus its wavelength. Since hair follicles and other dermatological targets are located deep in the dermis, depth penetration of the incident light is important. The output of the flashlamps is designed to generate a large amount of deep penetrating wavelengths. The majority of the output wavelengths 144 as shown in FIG. 7A of the flashlamps exhibit very good depth penetration as shown in an area 173 of the graph. This depth penetration allows incident light to reach deep dermatological targets and their components. Lower wavelengths 170 have very high melanin absorption FIG. 7B and blood absorption FIG. 7C, but have very little depth penetration 170. This makes low wavelengths well suited for shallow veins and pigmented based targets. Mid-wavelengths 171 have very low blood absorption FIG. 7B and medium melanin absorption FIG. 7A. These mid-wavelengths 171 are not good for veins, but work well for pigmented based targets and hair removal. The higher wavelengths 172 show little melanin and blood absorption FIG. 7B, 7C, but very deep penetration. These higher wavelengths 172 are well suited for deep melanin based targets at high energy and any dermatological targets that exist past 1 mm depth in the skin and tissue.

Figure 7E:
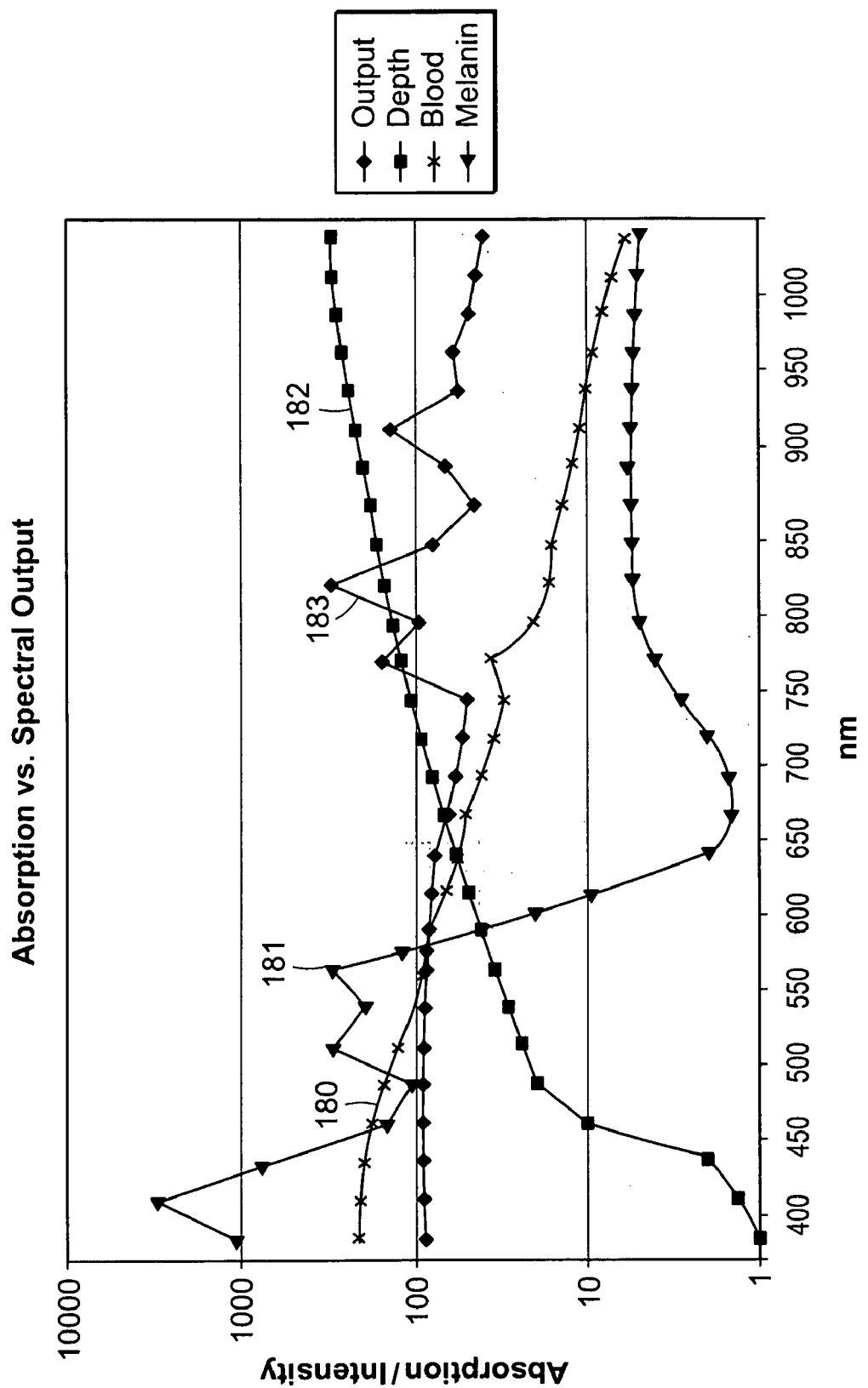
FIG. 7E shows blood absorption, melanin absorption, and depth penetration with respect to device wavelength output.

Referring to FIG. 7E that shows the spectral distribution 183 according to the invention as it corresponds to the absorption factors of different dermatological targets such as melanin 180, blood 181, and depth penetration 182. The spectral distribution pattern of the invention 183 covers all aspects of different dermatological chromophore absorptions throughout the spectrum that allows a multitude of various dermatological conditions to be treated with one all-encompassing wavelength output.

Figure 8:
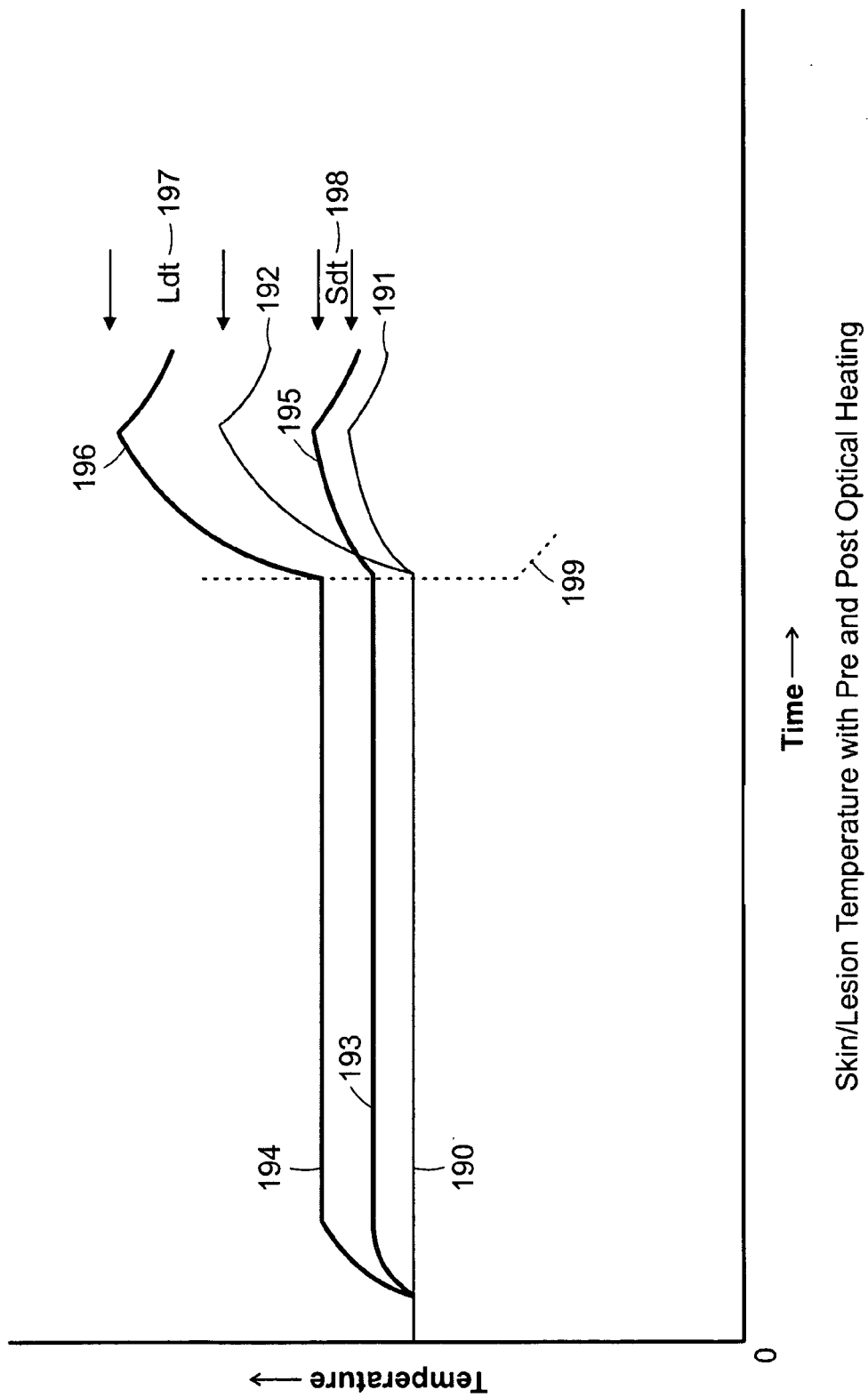
FIG. 8 shows temperature effect of pre/post optical lesion.

Turning to FIG. 8, the thermal effect of pre/post optical heating is depicted. Without pre/post optical heating the skin and lesion are at the same temperature 190 prior to pulse firing 199. During pulse firing, the skin increases in temperature 191 along with the lesion 192. The lesion temperature 192 is greater than the skin temperature 191 due to higher absorption of the light during the optical pulse. With pre/post optical heating, the lesion temperature 194 prior to pulse firing 199 is higher than the skin temperature 193. When the pulse fires 199 with pre/post optical heating, the lesion temperature 196 increases to a much higher level then without pre/post heating 192 due to the fact that the temperature of the lesion was higher before the pulse. The skin temperature 195 increases only slightly more after pulse firing 199 than without pre/post optical heating 191 since the skin has little absorption of light. The change of temperature of the skin 198 with and without pre/post optical heating is much less than the change of temperature of the lesion 197 with and without pre/post optical heating. The pre/post optical heating results an increased lesion temperature 196 and damage with minimum increase in skin temperature 195 and damage to provide more effective treatment results.

Although the apparatus described in the illustrative embodiment herein contains four flashlamps, it should be appreciated by those skilled in the art that the delivery head of the apparatus may contain more or less than four flashlamps depending on the application and the area of treatment. Similarly, the pulse train may consist of more or less than four pulses depending on the characteristic and severity of various dermatological conditions that are to be treated. In addition, the ratio and amount of krypton and xenon in the flashlamps may be altered to produce a slightly different wavelength output pattern or various light filters that are well known in the art may be used to eliminate unwanted wavelengths.

The foregoing has been a description of illustrative embodiments of the present invention. The present invention is not to be limited in scope by the illustrative embodiments described which are intended as specific illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims.

What is claimed:

1. A method for treating various dermatological conditions comprising the steps of:
    generating a light that has a specific wavelength distribution pattern output and intensity, said light being generated from multiple flashlamps;
    filtering said light through a first filter and a second filter to construct an optimum wavelength distribution pattern with said light;
    placing a hollow reflective light guide with a window against a skin section forming an optical seal to contain said light; and
    covering said skin section with a plume barrier lotion; and
    illuminating said skin section by directing said light through said first and second filters through said hollow reflective light guide through said plume barrier lotion.

2. The method according to claim 1, wherein said light has a specific pulse geometry.

3. The method according to claim 2, wherein said light generated a from multiple flashlamps which are fired simultaneously or consecutively with a delay between each said pulse.

4. The method according to claim 3, wherein said pulses from said flashlamps are approximately 14 ms in duration.

5. The method according to claim 4, wherein said flashlamps with progressive logarithmic spacing between said pulses to eliminate active skin cooling.

6. The method according to claim 3, wherein said flashlamps are individually powered by an electrical energy supply that is 160–400 joules for every $cm^2$ of output.

7. The method according to claim 1, wherein said light exiting said hollow light guide has a wavelength greater than 390 nm.

8. The method according to claim 1, wherein said light generated may be infused with a single wavelength laser source.

9. The method according to claim 1 wherein said light is non-laser and radially emitted and photons from said light are reflected from said hollow reflective light guide and exit through said first filter at multiple angles through said hollow reflective light guide and through said second filter for further desired wavelength cutoff and through said hollow reflective light guide into said skin section at multiple angles.

10. The method according to claim 1, wherein said light is generated from a light source comprising:
   a power source;
   a plurality of flashlamps;
   a water or air cooling system;
   a control source for firing said flashlamps with logarithmic spacing; and
   a laser rod head insertion for single wavelength infusion.

11. The method according to claim 10 wherein said flashlamps consist of Kr, Xe gas.

12. The method according to claim 10, wherein said control source allows simultaneous, overlap and consecutive firing of said flashlamps.

13. The method according to claim 10, wherein said flashlamps consist of synthetically fused quart doped with cerium oxide.

14. The method according to claim 1, wherein said hollow reflective light guide is made of ceramic.

15. The method according to claim 1 wherein said light spectral output pattern is generated in an output between 390 nm and 1,200 nm.

16. The method according to claim 1 wherein said light spectral output pattern is generated at a pulse firing rate dermatological lesion pre/post heating.

17. An apparatus for treating a dermatological condition comprising:
   a water cooled delivery head;
   at least one flashlamp contained within said delivery head wherein said at least one flashlamp produces a desired light output;
   an individual energy source connected to said at least one flashlamp;
   a control mechanism connected to said individual energy source said control mechanism allowing for consecutive firing of said at least one flashlamp;
   a laser rod inserted into the delivery head for single wavelength light infusion into said light output;
   a first light filter and a second light filter positioned beneath said delivery head wherein said first and second light filters eliminate selected wavelengths or portions thereof of said light; and
   a water cooled hollow reflective light guide directing said light to a treatment area.

18. The apparatus of claim 17 wherein said energy source is provided by battery power.

19. The apparatus of claim 17 wherein said energy source is able to deliver light through said at least one flashlamp for pre/post dermatological lesion heating.

20. The Apparatus of claim 17 wherein said laser rod is coated on both sides with a reflective coating the reflective wavelength of said reflective coating being matched to the wavelength of said laser rod.

* * * * *